(12) United States Patent
Faucette et al.

(10) Patent No.: US 9,489,816 B2
(45) Date of Patent: Nov. 8, 2016

(54) PORTABLE PATIENT MONITORING SYSTEM PROFILE SWITCHOVER

(75) Inventors: Richard Faucette, Andover, MA (US); Jason Braley, Andover, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 14/418,409

(22) PCT Filed: Jul. 31, 2012

(86) PCT No.: PCT/US2012/049066
§ 371 (c)(1),
(2), (4) Date: Jan. 29, 2015

(87) PCT Pub. No.: WO2014/021873
PCT Pub. Date: Feb. 6, 2014

(65) Prior Publication Data
US 2015/0243148 A1    Aug. 27, 2015

(51) Int. Cl.
*G08B 1/08* (2006.01)
*G08B 21/02* (2006.01)
*G06F 19/00* (2011.01)
*A61B 5/0205* (2006.01)
*G06F 1/16* (2006.01)
*A61B 5/00* (2006.01)

(52) U.S. Cl.
CPC .......... *G08B 21/02* (2013.01); *A61B 5/02055* (2013.01); *G06F 1/1632* (2013.01); *G06F 19/3406* (2013.01); *G06F 19/3412* (2013.01); *G06F 19/3418* (2013.01); *A61B 5/0002* (2013.01); *A61B 5/746* (2013.01); *A61B 2560/0266* (2013.01); *A61B 2560/0456* (2013.01)

(58) Field of Classification Search
CPC ................... A61B 5/0002; A61B 2560/0456; G06F 19/3418; G06F 19/3406
USPC .............. 340/539.12; 600/300, 301; 128/903
See application file for complete search history.

(56) References Cited

U.S. PATENT DOCUMENTS

| 5,640,953 | A | 6/1997 | Bishop et al. |
| 6,454,708 | B1 | 9/2002 | Ferguson et al. |
| 6,658,276 | B2 * | 12/2003 | Kianl .................. A61B 5/0002 600/322 |
| 7,316,648 | B2 | 1/2008 | Kelly et al. |
| 2011/0047298 | A1 | 2/2011 | Eaton et al. |
| 2011/0140896 | A1 | 6/2011 | Menzel |

OTHER PUBLICATIONS

International Search Report Issued in PCT/US2012/049066 dated Dec. 21, 2012.

* cited by examiner

*Primary Examiner* — John A Tweel, Jr.
(74) *Attorney, Agent, or Firm* — Jones Day

(57) ABSTRACT

Portable patient monitoring systems are provided that include profiles that can be selectively overwritten with profiles stored in or otherwise accessible by docking stations that can mate with the portable patient monitoring systems. Related apparatus, systems, techniques and articles are also described.

76 Claims, 3 Drawing Sheets

PORTABLE PATIENT MONITORING SYSTEM PROFILE SWITCHOVER

RELATED APPLICATION

This application is a National Stage Application under 35 U.S.C. 371 of PCT application number PCT/US2012/049066, titled, "Portable Patient Monitoring System Profile Switchover," filed Jul. 31, 2012. The disclosures of the aforementioned applications are hereby incorporated by reference in their entireties herein.

TECHNICAL FIELD

The subject matter described herein relates to selectively switching profiles used to specify one or more operational parameters of a portable patient monitoring system.

BACKGROUND

Portable patient monitoring systems, sometimes referred to simply as patient monitors, are important devices in clinical settings such as hospitals. The portable patient monitoring systems include and/or are in communication with one or more physiological sensors that continuously and/or periodically sense one or more physiological conditions of a patient. Caregivers often move such portable patient monitoring systems with a patient as he or she is moved within the hospital (e.g., from the emergency room to an operating room, etc.) by hand or using a transport device such as a gurney. Some portable patient monitoring systems can mechanically mate with docking stations that provide, when the portable patient monitors are docked, a power source and/or data communications.

Portable patient monitoring systems are typically programmable/customizable in that they allow for various settings such as alarm conditions to be adjusted. These settings can sometimes be lost when the portable patient monitoring systems are docked to a docking station and/or when a disruption such as a power failure occurs.

SUMMARY

In one aspect, a portable patient monitoring system is provided that can couple to at least one physiological sensor measuring physiological attributes of a patient. The portable patient monitoring system includes a display to display data characterizing the measured physiological attributes, at least one data processor, and memory for storing at least one profile specifying settings for a plurality of operational parameters of the patient monitoring system. In addition, the portable patient monitoring system is configured to dock with a docking station that in turn includes memory for storing at least one profile specifying settings for a plurality of operational parameters of a patient monitoring system. In response to detection of a docking event: (i) the profile stored in the memory of the portable patient monitoring system is overwritten with the profile stored in the memory of the docking station when the patient monitoring system is docked to the docking station and when certain conditions are not met, or (ii) the profile stored in the memory of the patient monitoring system continues to be used by the patient monitoring system when the patient monitoring system is docked to the docking station and when the certain conditions are met. While the portable patient monitoring system and the docking station can be used separately, in some cases, a system is provided that includes both the portable patient monitoring system and the docking station.

Each profile can include a profile identification (ID) that includes a profile checksum and a profile name. Each profile can include a profile identification (ID) that includes a unique identifier such as a globally unique identifier (a GUID), a concatenation of two or more values, a hash of one or more values, and the like. The profile name can include a unique identifier that corresponds to the docking station.

The certain conditions can be determined as being met when the profile ID of the docking station matches the profile ID of the patient monitoring system. The display can provide a visual indication when the profile stored in the memory of the portable patient monitoring system is overwritten with the profile stored in the memory of the docking station. The portable patient monitoring system can include an interface that provides a prompt seeking user-generated input to approve the overwriting of the profile in the portable patient monitoring system with the profile stored in the memory of the docking station.

In some implementations the portable patient monitoring system and/or the docking station can store two or more profiles. User-generated input and/or contextual data can be used to determine which of the two or more profiles to use by the portable patient monitoring system. The docking station can be coupled to a communications network for updating the profile stored in the memory of the docking station.

The operational parameters of the portable patient monitoring system can vary. Example parameters include, but are not limited to: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

The docking event can be a mechanical mating of the portable patient monitoring system with the docking station and/or a power cycle by one or more of the portable patient monitoring system or the docking station.

In an interrelated aspect, a method is provided in which a docking event is detected. Thereafter, a profile stored in the memory of the portable patient monitoring system is overwritten with the profile stored in the memory of the docking station when the patient monitoring system is docked to the docking station and when certain conditions are not met, or alternatively, the profile stored in the memory of the patient monitoring system is maintained and used by the patient monitoring system when the patient monitoring system is docked to the docking station and when the certain conditions are met.

In a further interrelated aspect, a portable patient monitoring system is provided that can couple to at least one physiological sensor measuring physiological attributes of a patient. Similar to above, the portable patient monitoring system includes a display to display data characterizing the measured physiological attributes, at least one data processor, and memory for storing at least one profile specifying settings for a plurality of operational parameters of the patient monitoring system. In addition, the portable patient monitoring system is configured to dock to a docking station. The docking station is coupled to a remote computing system that comprises memory storing at least one profile specifying settings for a plurality of operational parameters of a patient monitoring system.

Upon detection of a docking event, the profile stored in the memory of the portable patient monitoring system is overwritten with the profile stored in the memory of the remote computing system coupled to the docking station when the patient monitoring system and when certain conditions are not met, or alternatively, the profile stored in the memory of the patient monitoring system continues to be used by the patient monitoring system when the patient monitoring system and when the certain conditions are met.

Computer program products are also described that comprise non-transitory computer readable media storing instructions, which when executed by at least one data processor of one or more computing systems, causes the at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The subject matter described herein provides many advantages. For example, by providing certain rules/conditions for maintaining patient specific settings as a patient monitoring system is docked to one or more docking stations (or other events occur), caregivers can focus on other activities relating to the wellbeing of the patient or other patients.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
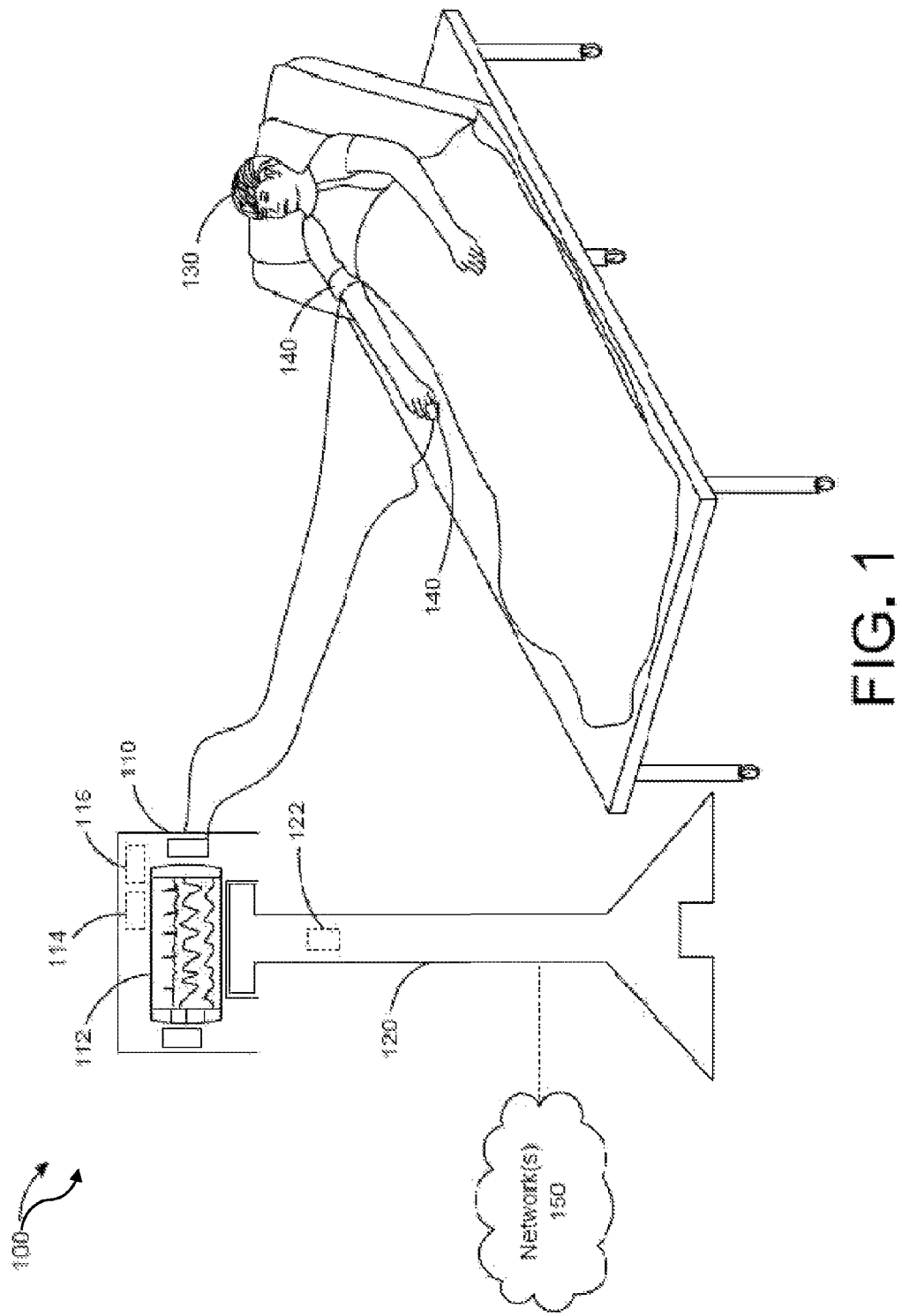
FIG. 1 is a system diagram illustrating a portable patient monitoring system with a docking station in a clinical setting.

FIG. 1 is a diagram 100 illustrating a portable patient monitoring system 110 coupled to a docking station 120 (note that various aspects of the diagram are not to scale). The portable patient monitoring system 110 can be physically coupled and decoupled to the docking station 120 by one or more caregivers. The portable patient monitoring system 110 is coupled (either by fixed wires or wirelessly) to one or more physiological sensors 140 that characterize various physiological parameters (e.g., ECG, basic arrhythmia, respiration, pulse rate, temperature, noninvasive blood pressure, SpO2, etc.) of a patient 130.

One example of a portable patient monitoring system is the Dräger Infinity Gamma XL vital signs monitor. The portable patient monitoring system 110 includes an interface 112 providing visual and/or audio feedback based on data received from the physiological sensors 140. The interface 112 (via a touch-screen interface, one or more buttons or knobs, and/or a keyboard, etc.) can also act as a portal by which a caregiver can modify one or more operational parameters of the portable patient monitoring system 110. The operational parameters can be any of a variety of settings including, but not limited to: alarm thresholds, patient information (e.g., name, sex, weight, age, etc.), patient category (e.g., adult, pediatric or neonate, etc.), speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, bar graph on/off and the like. The collection of settings used to define how the portable patient monitoring system 110 operates are each referred to herein as "profiles".

The portable patient monitoring system 110 also includes at least one data processor 114 and memory 116 for storing data. The memory 116 can store, for example, one or more profiles associated with the portable patient monitoring system 110 and/or one or more patients. The docking station 120 also includes memory 122 that can store one or more profiles. In some cases, there can be multiple profiles for a particular type of portable patient monitoring system and ranking rules can be utilized to determine which of such profiles can be transferred to the portable patient monitoring system 110 and under which conditions such transfers occur. Some docking stations 120 can be coupled to a communications network 150 such as an intranet or the Internet. Such network(s) 150 can be used to access remote computing systems to update or otherwise change the profiles stored within the memory 122 of the docking stations 120 or alternatively remote computing systems coupled via the network(s) 150 can store profiles (as opposed to memory 122). The networks 150 can also be used to convey data characterizing the patient's physiological measurements as sensed by the physiological sensors 140.

As will be described in further detail below, upon the occurrence of a docking event (e.g., the portable patient monitoring system 110 being mated/coupled to the docking station 120), the portable patient monitoring system 110 and/or the docking station 120 determines whether one or more conditions have been met. Based on such determination, the profile utilized by the portable patient monitoring system 110 can be changed to either a different profile stored in the memory 116 of the portable patient monitoring system 110 or to a profile stored in the memory 122 of the docking station 120 (or alternatively from a remote computing system coupled to the docking station 120 via network (150)).

The memory 116 can provide persistent storage locations for a profile checksum (having, for example, a factory default value of zero) and a profile name (referencing a profile stored in the memory 116). A profile checksum is a digit (or digits) that represents a sum of the values that represent some or all of the profile settings. The profile name can be part of the profile (similar to a profile name string) that is provided when the profile is created or it can be a number that is unique to the docking station that stores the profile (e.g., a MAC address). As used herein, the profile checksum and the profile name combined together is referred to as the profile identification or "profile ID". Even if two profiles contain the exact same settings (and thus each have the same checksum) they can still be detected as having different profile IDs if their profile names are different. It will be appreciated that a profile ID can be any unique identifier—or in some cases, a substantially unique identifier. For example, the profile ID can be comprised of two values other than a profile checksum and profile name and/or the profile ID can include less than two values or more than two values (which may include the profile checksum and/or the profile name). In some implementations, unique identifiers such as a GUID (globally unique identifier), a concatenation of two or more values, or a hash of one or more values can be used.

When a caregiver makes a change to a profile setting on the portable patient monitoring system 110, the profile ID does not change. Modifications to one or more operating parameters of the patient monitoring system 110 after a profile has been loaded (which specifies settings for the operating parameters) can be referred to as "patient specific settings". These patient specific settings can be stored in the memory 116 of the portable patient monitoring system 110.

When the portable patient monitoring system 110 is docked to a docking station 120, the profile ID of the profile stored inside the docking station 120 can be made available to the portable patient monitoring system 110. That is data for the profile stored in the memory 122 of the docking station 120 is transferred (for example, via a communications link) to the memory 116 of the portable patient monitoring system 110. The portable patient monitoring system 110 can then compare a profile ID stored in the memory 116 to the one from the docking station for equality. If the profile IDs are equal, then the profile from the docking station 120 shall not be loaded into and/or used by the portable patient monitoring system 110 and the patient specific settings (stored in the memory 116 of the portable patient monitoring system 110) shall be preserved. If the profile IDs are not equal, then the profile from the memory 122 of the docking station 120 shall be loaded into the memory 116 of the portable patient monitoring system 110 which causes the portable patient monitoring system 110 to overwrite any patient specific settings.

Groups of docking station 120 have different profiles which reflect how the portable patient monitoring systems 110 should be differently configured. For example, a particular patient area (e.g., bedside, operating room, etc.) can have more than one associated docking station 120 such that moving the portable patient monitoring system 110 among such docking stations 120 results in similar results (e.g., the same profile is loaded from the docking stations 120 and/or the current profile used by the portable patient monitoring system 110 is maintained, etc.). The docking stations 120 can be coupled directly via a communications link (e.g., peer-to-peer wireless connection, wireless network connection, intranet, Internet, etc.) so that the profiles stored in their respective memories 122 can be updated and/or coordinated.

In cases in which there are multiple profiles stored in either of the memory 116 of the portable patient monitoring system 110 and the memory 122 of the docking station 120, contextual data can be used to determine which profile to use at any given time. Such contextual data can be user-specified preferences (whether in advance of docketing or subsequent to docketed), patient data (e.g., age, sex, condition, etc.) and/or based on one or more sensed physiological conditions (e.g., heart rate over a certain level, blood pressure below a certain level, etc.).

In some implementations, the interface 112 can include an indication showing that the profile currently utilized by the portable patient monitoring system 110 is about to change to the profile stored in the docking station 120. The interface 112 can seek approval of such a change (via a prompt, etc.) from a user.

Figure 2:
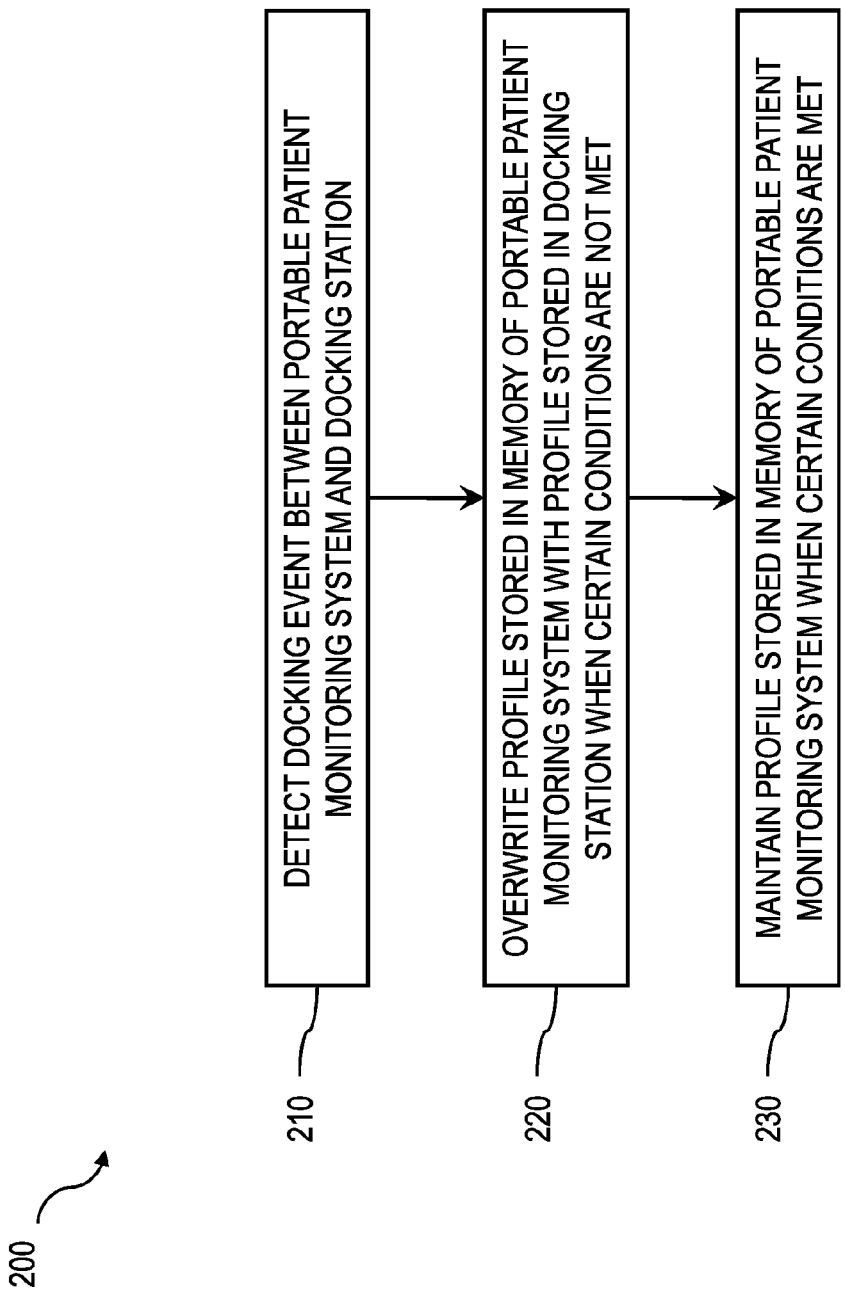
FIG. 2 is a first process flow diagram illustrating switchover of profiles used by a portable patient monitoring system as in FIG. 1.

FIG. 2 is a process flow diagram 200 illustrating a method in which, at 210, a docking event is detected between a portable patient monitoring system and a docking station. Thereafter, at 220, a profile stored in memory of the portable patient monitoring system is overwriting with the profile stored in memory of the docking station when the patient monitoring system is docked to the docking station and when certain conditions are not met. Otherwise, at 230, the profile stored in the memory of the patient monitoring system and used by the patient monitoring system is maintained when the patient monitoring system is docked to the docking station and when the certain conditions are met.

Figure 3:
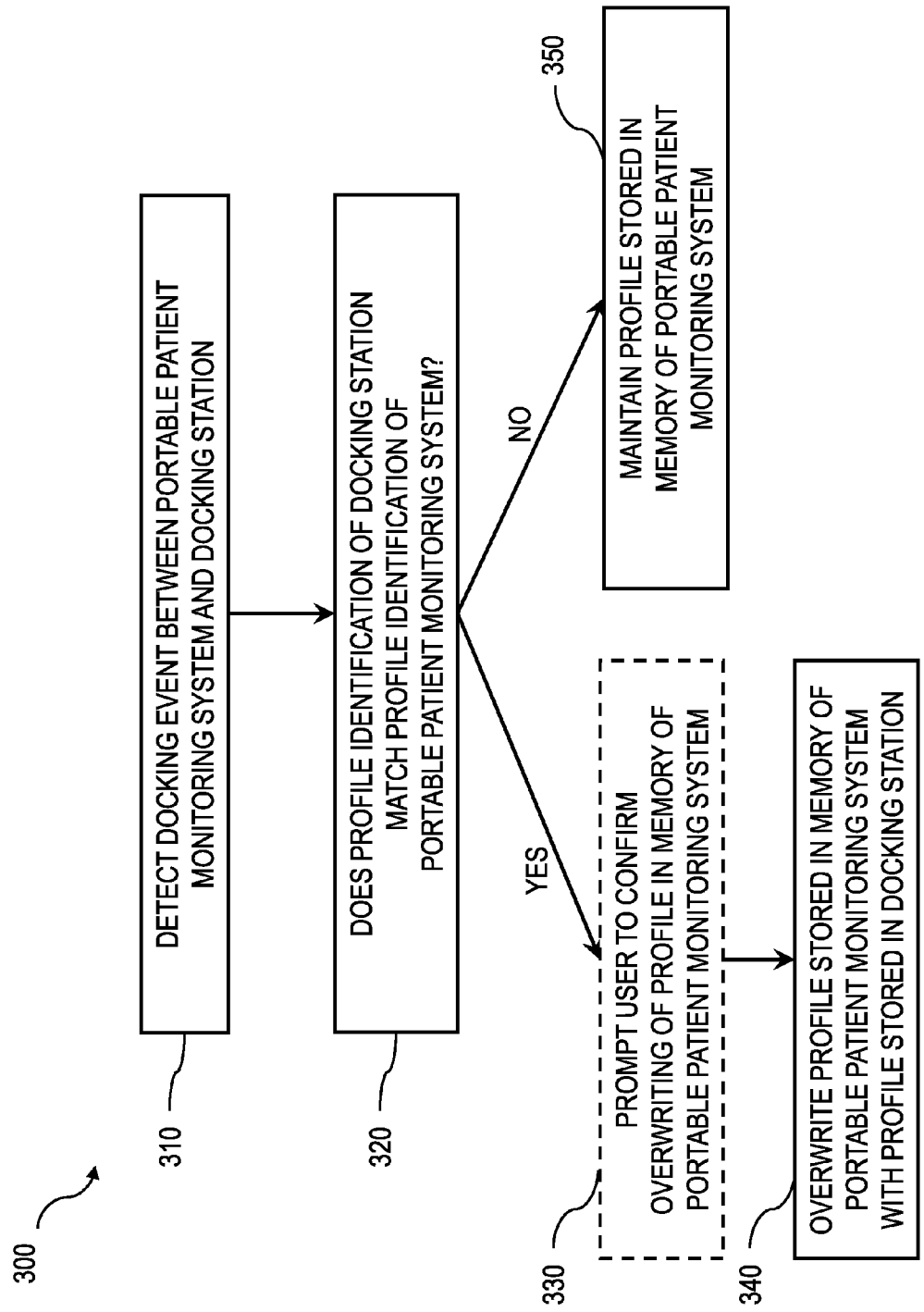
FIG. 3 is a second process flow diagram illustrating switchover of profiles used by a portable patient monitoring system as in FIG. 1.

FIG. 3 is a process flow diagram 300 illustrating a method in which, at 310, a docking event is detected between a portable patient monitoring system and a docking station. Thereafter, at 320, it is determined whether the profile identification of the docking station matches the profile identification of the portable patient monitoring system. If the profile identifications match, at 340, the profile stored in the memory of the portable patient monitoring system is overwritten with the profile stored in the memory of the docking station. In some variations, the user can be prompted (e.g., via the display/interface 112, etc), at 330, to confirm whether the portable patient monitoring system profile should be overwritten. If the profile identifications do not match, then, at 350, the profile stored in the memory of the portable patient monitoring system is maintained.

Example Use Scenarios

In a first example, a brand new portable patient monitoring system 110 is docked to a docking station 120 that has a profile stored inside its respective memory 122. The resulting action shall be that the portable patient monitoring system 110 loads the profile from the docking station 120 into its memory 116 and uses such profile to define which settings/operational parameters will be active/used.

In a second example, a portable patient monitoring system 110 has a profile from a first docking station 120 in the emergency room (ER) ward of the hospital stored in its memory 116 and is subsequently docked to a second docking station 120 in the operating room (OR) ward of the hospital. The profile IDs of the currently utilized profile of the portable patient monitoring system 110 and the second docking station 120 are not equal. Therefore, the portable patient monitoring system 110 loads the profile from the memory 122 of the second docking station 120 from its respective memory 122. All profile settings from the ER ward and any patient specific settings shall be overwritten in the memory 116 of the portable patient monitoring system 110.

In a further example, a portable patient monitoring system 110 that contains a profile from a first docking station 120 in the ER ward of the hospital in its respective memory 116 is subsequently docked to a second docking station 120 in the ER ward of the hospital. In this case, a profile name is part of the profile, and as such, the profile IDs are equal. There will be no resulting action and any patient specific settings shall be preserved. If the profile name is unique to the second docking station 120 in this scenario, then the profile IDs will not be equal. In such a case, all profile settings from the first docking station 120 and any patient specific settings shall be overwritten in the memory 116 of the portable patient monitoring system 110.

In yet another example, a portable patient monitoring system 110 that contains a profile from a first docking station 120 in the ER ward of the hospital is docked to a second docking station 120 that contains no profile. There will be no resulting action and any patient specific settings shall be preserved in the memory 116 of the portable patient monitoring system 110.

In still a further example, a portable patient monitoring system 110 that has a profile in its memory 116 that was received from a first docking station 120 to which it is currently docked, is subsequently un-docked by a caregiver (i.e., the clinical staff, etc.). The caregiver then inputs some patient specific settings and re-docks the portable patient monitoring system 110 to the docking station 120. In this scenario, the profile IDs will be equal. There will be no resulting action and the patient specific settings shall be preserved.

In another example, a portable patient monitoring system 110 that contains a profile in its memory 116 that was received from a docking station 120 that it is currently docked to experiences a power cycle of the docking station 120. There will be no resulting action and any patient specific settings shall be preserved. In some implementations, a power cycle can be characterized as/equal to a dock event by the portable patient monitoring system 110. Causes of a docking station power cycle can include, for example, electrical loss in the building, someone unplugging and re-plugging power to the docking station 120 or a software fault in the docking station 120.

In still another example, a portable patient monitoring system 110 contains a profile stored in its memory 116 that was received from a docking station 120 to which it is currently docked to experiences a power cycle. There will be no resulting action and any patient specific settings shall be preserved. The power cycle can be perceived as a dock event by a portable patient monitoring system 110. Causes of a portable patient monitoring system power cycle can include intentional user actions, and a hardware and/or software fault in the docking stations 120 and/or the portable patient monitoring system 110.

Various implementations and aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium (e.g., a non-transitory machine-readable medium, etc.) that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figure(s) and described herein do not require the particular order shown, or sequential order, to achieve desirable results. Other embodiments may be within the scope of the following claims.

What is claimed is:

1. A system comprising:
   a portable patient monitoring system to couple to at least one physiological sensor measuring physiological attributes of a patient, the portable patient monitoring system comprising a display to display data characterizing the measured physiological attributes, at least one data processor, and memory for storing at least one profile specifying settings for a plurality of operational parameters of the patient monitoring system, the portable patient monitoring system configured to dock with a docking station, the docking station comprising memory for storing at least one profile specifying settings for a plurality of operational parameters of a patient monitoring system; wherein in response to detection of a docking event, and without human intervention:
   the profile stored in the memory of the portable patient monitoring system is overwritten with the profile stored in the memory of the docking station when the patient monitoring system is docked to the docking station and when certain conditions are not met, and
   the profile stored in the memory of the patient monitoring system continues to be used by the patient monitoring system when the patient monitoring system is docked to the docking station and when the certain conditions are met;
   wherein the docking event is a power cycle by one or more of the portable patient monitoring system or the docking station.

2. A system as in claim 1, further comprising the docking station.

3. A system as in claim 1, wherein each profile comprises a profile identification (ID) that includes a profile checksum and a profile name.

4. A system as in claim 1, wherein each profile comprises a profile identification (ID) that includes a unique identifier.

5. A system as in claim 4, wherein the unique identifier is selected from a group consisting of: a globally unique identifier, a concatenation of two or more values, and a hash of one or more values.

6. A system as in claim 3, wherein the profile name comprises a unique identifier corresponding to the docking station.

7. A system as in claim 3, wherein the certain conditions are met when the profile ID of the docking station matches the profile ID of the patient monitoring system.

8. A system as in claim 1, wherein the display provides a visual indication when the profile stored in the memory of the portable patient monitoring system is overwritten with the profile stored in the memory of the docking station.

9. A system as in claim 8, wherein the portable patient monitoring system comprises an interface that provides a prompt seeking user-generated input to approve the overwriting of the profile in the portable patient monitoring system with the profile stored in the memory of the docking station.

10. A system as in claim 1, wherein one or more of the portable patient monitoring system and the docking station stores two or more profiles.

11. A system as in claim 10, wherein contextual data is used to determine which of the two or more profiles to use by the portable patient monitoring system.

12. A system as in claim 1, wherein the docking station is coupled to a communications network for updating the profile stored in the memory of the docking station.

13. A system as in claim 1, wherein the operational parameters are selected from a group consisting of: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

14. A method for implementation by one or more data processors forming part of at least one computing device and without human intervention, the method comprising:
   detecting, by at least one data processor, a docking event between a portable patient monitoring system and a docking station,
   wherein the portable patient monitoring system is coupled to at least one physiological sensor measuring physiological attributes of a patient and comprises a display to display data characterizing the measured physiological attributes, at least one data processor, and memory for storing at least one profile specifying settings for a plurality of operational parameters of the patient monitoring system; and
   wherein the docking station is configured to receive the portable patient monitoring system and comprises memory for storing at least one profile specifying settings for a plurality of operational parameters of a patient monitoring system;
   overwriting, by at least one data processor, a profile stored in the memory of the portable patient monitoring system with the profile stored in the memory of the docking station when certain conditions are not met; and
   maintaining, by at least one data processor, the profile stored in the memory of the patient monitoring system and used by the patient monitoring system when the certain conditions are met;
   wherein the docking event is a mechanical mating of the portable patient monitoring system with the docking station.

15. A method as in claim 14, wherein each profile comprises a profile identification (ID) that includes a profile checksum and a profile name.

16. A method as in claim 14, wherein each profile comprises a profile identification (ID) that includes a unique identifier.

17. A method as in claim 16, wherein the unique identifier is selected from a group consisting of: a globally unique identifier, a concatenation of two or more values, and a hash of one or more values.

18. A method as in claim 15, wherein the profile name comprises a unique identifier corresponding to the docking station.

19. A method as in claim 15, wherein the certain conditions are met when the profile ID of the docking station matches the profile ID of the patient monitoring system.

20. A method as in claim 14 further comprising: displaying a visual indication in the display when the profile stored in the memory of the portable patient monitoring system is overwritten with the profile stored in the memory of the docking station.

21. A method as in claim 20 further comprising:
   prompting, via an interface of the portable patient monitoring system, a user to approve the overwriting of the profile in the portable patient monitoring system with the profile stored in the memory of the docking station.

22. A method as in claim 14, wherein one or more of the portable patient monitoring system and the docking station stores two or more profiles.

23. A method as in claim 22, wherein contextual data is used to determine which of the two or more profiles to use by the portable patient monitoring system.

24. A method as in claim 14, wherein the docking station is coupled to a communications network for updating the profile stored in the memory of the docking station, the method further comprising:
   accessing, by the docking station, a remote computing system via the communications network in response to the docking event.

25. A method as in claim 14, wherein the operational parameters are selected from a group consisting of: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

26. A system comprising:
   a docking station configured to dock with a portable patient monitoring system, the docking station comprising memory for storing at least one profile specifying settings for a plurality of operational parameters of a patient monitoring system, the portable patient monitoring system being configured to couple to at least one physiological sensor measuring physiological attributes of a patient, the portable patient monitoring system comprising a display to display data characterizing the measured physiological attributes, at least one data processor, and memory for storing at least one profile specifying settings for a plurality of operational parameters of the patient monitoring system;
   wherein in response to detection of a docking event and without human intervention:

the profile stored in the memory of the portable patient monitoring system is overwritten with the profile stored in the memory of the docking station when the patient monitoring system is docked to the docking station and when certain conditions are not met, and the profile stored in the memory of the patient monitoring system continues to be used by the patient monitoring system when the patient monitoring system is docked to the docking station and when the certain conditions are met;

wherein the docking event is a power cycle by one or more of the portable patient monitoring system or the docking station.

27. A system as in claim 26, further comprising the portable patient monitoring system.

28. A system as in claim 26, wherein each profile comprises a profile identification (ID) that includes a profile checksum and a profile name.

29. A system as in claim 26, wherein each profile comprises a profile identification (ID) that includes a unique identifier.

30. A system as in claim 29, wherein the unique identifier is selected from a group consisting of: a globally unique identifier, a concatenation of two or more values, and a hash of one or more values.

31. A system as in claim 28, wherein the profile name comprises a unique identifier corresponding to the docking station.

32. A system as in claim 28, wherein the certain conditions are met when the profile ID of the docking station matches the profile ID of the patient monitoring system.

33. A system as in claim 26, wherein the display provides a visual indication when the profile stored in the memory of the portable patient monitoring system is overwritten with the profile stored in the memory of the docking station.

34. A system as in claim 33, wherein the portable patient monitoring system comprises an interface that provides a prompt seeking user-generated input to approve the overwriting of the profile in the portable patient monitoring system with the profile stored in the memory of the docking station.

35. A system as in claim 26, wherein one or more of the portable patient monitoring system and the docking station stores two or more profiles.

36. A system as in claim 35, wherein contextual data is used to determine which of the two or more profiles to use by the portable patient monitoring system.

37. A system as in claim 26, wherein the docking station is coupled to a communications network for updating the profile stored in the memory of the docking station.

38. A system as in claim 26, wherein the operational parameters are selected from a group consisting of: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

39. A system comprising:

a portable patient monitoring system to couple to at least one physiological sensor measuring physiological attributes of a patient, the portable patient monitoring system comprising a display to display data characterizing the measured physiological attributes, at least one data processor, and memory for storing at least one profile specifying settings for a plurality of operational parameters of the patient monitoring system, the portable patient monitoring system configured to dock with a docking station, the docking station comprising memory for storing at least one profile specifying settings for a plurality of operational parameters of a patient monitoring system; wherein in response to detection of a docking event, and without human intervention:

the profile stored in the memory of the portable patient monitoring system is overwritten with the profile stored in the memory of the docking station when the patient monitoring system is docked to the docking station and when certain conditions are not met, and the profile stored in the memory of the patient monitoring system continues to be used by the patient monitoring system when the patient monitoring system is docked to the docking station and when the certain conditions are met;

wherein the docking event is a mechanical mating of the portable patient monitoring system with the docking station.

40. A system as in claim 39, further comprising the docking station.

41. A system as in claim 39, wherein each profile comprises a profile identification (ID) that includes a profile checksum and a profile name.

42. A system as in claim 39, wherein each profile comprises a profile identification (ID) that includes a unique identifier.

43. A system as in claim 42, wherein the unique identifier is selected from a group consisting of: a globally unique identifier, a concatenation of two or more values, and a hash of one or more values.

44. A system as in claim 41, wherein the profile name comprises a unique identifier corresponding to the docking station.

45. A system as in claim 41, wherein the certain conditions are met when the profile ID of the docking station matches the profile ID of the patient monitoring system.

46. A system as in claim 39, wherein the display provides a visual indication when the profile stored in the memory of the portable patient monitoring system is overwritten with the profile stored in the memory of the docking station.

47. A system as in claim 46, wherein the portable patient monitoring system comprises an interface that provides a prompt seeking user-generated input to approve the overwriting of the profile in the portable patient monitoring system with the profile stored in the memory of the docking station.

48. A system as in claim 39, wherein one or more of the portable patient monitoring system and the docking station stores two or more profiles.

49. A system as in claim 48, wherein contextual data is used to determine which of the two or more profiles to use by the portable patient monitoring system.

50. A system as in claim 39, wherein the docking station is coupled to a communications network for updating the profile stored in the memory of the docking station.

51. A system as in claim 39, wherein the operational parameters are selected from a group consisting of: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

52. A method for implementation by one or more data processors forming part of at least one computing device and without human intervention, the method comprising:
- detecting, by at least one data processor, a docking event between a portable patient monitoring system and a docking station,
- wherein the portable patient monitoring system is coupled to at least one physiological sensor measuring physiological attributes of a patient and comprises a display to display data characterizing the measured physiological attributes, at least one data processor, and memory for storing at least one profile specifying settings for a plurality of operational parameters of the patient monitoring system; and
- wherein the docking station is configured to receive the portable patient monitoring system and comprises memory for storing at least one profile specifying settings for a plurality of operational parameters of a patient monitoring system;
- overwriting, by at least one data processor, a profile stored in the memory of the portable patient monitoring system with the profile stored in the memory of the docking station when certain conditions are not met; and
- maintaining, by at least one data processor, the profile stored in the memory of the patient monitoring system and used by the patient monitoring system when the certain conditions are met;
- wherein the docking event is a power cycle by one or more of the portable patient monitoring system or the docking station.

53. A method as in claim 52, wherein each profile comprises a profile identification (ID) that includes a profile checksum and a profile name.

54. A method as in claim 52, wherein each profile comprises a profile identification (ID) that includes a unique identifier.

55. A method as in claim 54, wherein the unique identifier is selected from a group consisting of: a globally unique identifier, a concatenation of two or more values, and a hash of one or more values.

56. A method as in claim 52, wherein the profile name comprises a unique identifier corresponding to the docking station.

57. A method as in claim 52, wherein the certain conditions are met when the profile ID of the docking station matches the profile ID of the patient monitoring system.

58. A method as in claim 52 further comprising: displaying a visual indication in the display when the profile stored in the memory of the portable patient monitoring system is overwritten with the profile stored in the memory of the docking station.

59. A method as in claim 58 further comprising: prompting, via an interface of the portable patient monitoring system, a user to approve the overwriting of the profile in the portable patient monitoring system with the profile stored in the memory of the docking station.

60. A method as in claim 52, wherein one or more of the portable patient monitoring system and the docking station stores two or more profiles.

61. A method as in claim 60, wherein contextual data is used to determine which of the two or more profiles to use by the portable patient monitoring system.

62. A method as in claim 52, wherein the docking station is coupled to a communications network for updating the profile stored in the memory of the docking station, the method further comprising:
- accessing, by the docking station, a remote computing system via the communications network in response to the docking event.

63. A method as in claim 52, wherein the operational parameters are selected from a group consisting of: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

64. A system comprising:
- a docking station configured to dock with a portable patient monitoring system, the docking station comprising memory for storing at least one profile specifying settings for a plurality of operational parameters of a patient monitoring system, the portable patient monitoring system being configured to couple to at least one physiological sensor measuring physiological attributes of a patient, the portable patient monitoring system comprising a display to display data characterizing the measured physiological attributes, at least one data processor, and memory for storing at least one profile specifying settings for a plurality of operational parameters of the patient monitoring system;
- wherein in response to detection of a docking event and without human intervention:
  - the profile stored in the memory of the portable patient monitoring system is overwritten with the profile stored in the memory of the docking station when the patient monitoring system is docked to the docking station and when certain conditions are not met, and
  - the profile stored in the memory of the patient monitoring system continues to be used by the patient monitoring system when the patient monitoring system is docked to the docking station and when the certain conditions are met;
- wherein the docking event is a mechanical mating of the portable patient monitoring system with the docking station.

65. A system as in claim 64, further comprising the portable patient monitoring system.

66. A system as in claim 64, wherein each profile comprises a profile identification (ID) that includes a profile checksum and a profile name.

67. A system as in claim 64, wherein each profile comprises a profile identification (ID) that includes a unique identifier.

68. A system as in claim 67, wherein the unique identifier is selected from a group consisting of: a globally unique identifier, a concatenation of two or more values, and a hash of one or more values.

69. A system as in claim 68, wherein the profile name comprises a unique identifier corresponding to the docking station.

70. A system as in claim 66, wherein the certain conditions are met when the profile ID of the docking station matches the profile ID of the patient monitoring system.

71. A system as in claim 64, wherein the display provides a visual indication when the profile stored in the memory of the portable patient monitoring system is overwritten with the profile stored in the memory of the docking station.

72. A system as in claim 71, wherein the portable patient monitoring system comprises an interface that provides a prompt seeking user-generated input to approve the overwriting of the profile in the portable patient monitoring system with the profile stored in the memory of the docking station.

73. A system as in claim 64, wherein one or more of the portable patient monitoring system and the docking station stores two or more profiles.

74. A system as in claim 73, wherein contextual data is used to determine which of the two or more profiles to use by the portable patient monitoring system.

75. A system as in claim 64, wherein the docking station is coupled to a communications network for updating the profile stored in the memory of the docking station.

76. A system as in claim 64, wherein the operational parameters are selected from a group consisting of: alarm thresholds, patient information, patient category, speaker volume, alarm delay, pacer mode, parameter color, heart rate source, tone source, tone volume, vertical scale of waveform, ECG filtering on/off, invasive blood pressure filtering on/off, pacer detection on/off, QRS sync marker on/off, and bar graph on/off.

* * * * *